(12) United States Patent
Blurton et al.

(10) Patent No.: US 6,559,166 B1
(45) Date of Patent: May 6, 2003

(54) PHENYLSULPHONYL DERIVATIVES AS 5-HT RECEPTOR LIGANDS

(75) Inventors: Peter Blurton, Welwyn Garden City (GB); Frank Burkamp, Bishops Stortford (GB); Susan Koon-Fung Cheng, Bietigheim-Bissingen, DE (US); Stephen Robert Fletcher, Bishops Stortford (GB); Angus Murray MacLeod, Bishops Stortford (GB); Daniel Spinks, Motherwell (GB); Monique Bodil Van Niel, Welwyn Garden City (GB)

(73) Assignee: Merck Sharp & Dohme Ltd., Hoddesdon ( * ) Notice: Subject to any disclaimer, the term of this patent is extended or adjusted under 35 U.S.C. 154(b) by 0 days.

(21) Appl. No.: 09/889,702

(22) PCT Filed: Jan. 11, 2000

(86) PCT No.: PCT/GB00/00153

§ 371 (c)(1),
(2), (4) Date: Sep. 27, 2001

(87) PCT Pub. No.: WO00/43362

PCT Pub. Date: Jul. 27, 2000

(30) Foreign Application Priority Data

Jan. 19, 1999 (GB) ............................................. 99011470

(51) Int. Cl.[7] ..................... A61K 31/445; C07D 211/54; C07D 211/30
(52) U.S. Cl. ........................................ 514/327; 546/217
(58) Field of Search ........................... 546/217; 514/327

(56) References Cited

U.S. PATENT DOCUMENTS

| | | | |
|---|---|---|---|
| 4,128,552 A | 12/1978 | Wise et al. | |
| 4,218,455 A | 8/1980 | Wise et al. | |
| 4,977,165 A | 12/1990 | Oinuma et al. | |
| 5,082,850 A | 1/1992 | Oinuma et al. | |
| 5,162,347 A | 11/1992 | Oinuma et al. | |
| 5,246,946 A | 9/1993 | Oinuma et al. | |
| 5,272,160 A | * 12/1993 | Chenard ..................... | 514/327 |
| 5,418,242 A | 5/1995 | Bru-Magniez et al. | |
| 5,753,679 A | 5/1998 | Riemer | |

FOREIGN PATENT DOCUMENTS

| | | |
|---|---|---|
| DE | 19601189 | 7/1997 |
| EP | 0261688 | 3/1988 |
| EP | 0304888 | 3/1989 |
| EP | 0330826 | 9/1989 |
| WO | 91/18602 | 12/1991 |
| WO | 96/35666 | 11/1996 |

* cited by examiner

*Primary Examiner*—Alan L. Rotman
*Assistant Examiner*—Rita Desai
(74) *Attorney, Agent, or Firm*—James L. McGinnis; Melvin Winokur

(57) ABSTRACT

A class of phenylsulphonyl derivatives wherein the sulphonyl moiety is also attached to an N-arylalkyl-substituted azetidine, pyrrolidine or piperidine ring are selective antagonists of the human 5-$HT_{2A}$ receptor and are therefore useful as pharmaceutical agents, especially in the treatment and/or prevention of adverse conditions of the central nervous system, including schizophrenia and depression.

7 Claims, No Drawings

PHENYLSULPHONYL DERIVATIVES AS 5-HT RECEPTOR LIGANDS

This application is a §371 National Stage filing of PCT/GB00/00153, which was filed on Jan. 11, 2000, and was published as WO 00/43362 on Jul. 27, 2000.

The present invention relates to a class of sulphonyl derivatives which act on serotonin receptors (also known as 5-hydroxytryptamine or 5-HT receptors). More particularly, the invention concerns phenylsulphonyl derivatives wherein the sulphonyl moiety is also attached to an N-arylalkyl-substituted azetidine, pyrrolidine or piperidine ring. These compounds are selective antagonists of the human 5-HT$_{2A}$ receptor and are therefore useful as pharmaceutical agents, especially in the treatment and/or prevention of adverse conditions of the central nervous system, including psychotic disorders such as schizophrenia.

Schizophrenia is a disorder which is conventionally treated with drugs known as neuroleptics. In many cases, the symptoms of schizophrenia can be treated successfully with so-called "classical" neuroleptic agents such as haloperidol. Classical neuroleptics generally are antagonists at dopamine D$_2$ receptors.

Notwithstanding their beneficial antipsychotic effects, classical neuroleptic agents such as haloperidol are frequently responsible for eliciting acute extrapyramidal symptoms (movement disorders) and neuroendocrine (hormonal) disturbances. These side-effects, which plainly detract from the clinical desirability of classical neuroleptics, are believed to be attributable to D$_2$ receptor blockade in the striatal region of the brain.

The compound (+)-α-(2,3-dimethoxyphenyl)-1-[2-(4-fluorophenyl)ethyl]-4-piperidinemethanol (also known as MDL-100,907) is described in WO 91/18602. In preclinical studies, MDL-100,907 failed to induce catalepsy and failed to block apomorphine-induced stereotyped behaviour in animal models, strongly suggesting that this compound would be free from any liability to cause extrapyramidal side-effects. MDL-100,907 is currently undergoing clinical trials in schizophrenic patients and has demonstrated efficacy in a multicentre, placebo-controlled study for antipsychotic potential, with no neurological adverse effects. Pharmacologically, MDL-100,907 has been shown to be a potent antagonist of human 5-HT$_{2A}$ receptors, whilst being essentially devoid of activity at the human dopamine D$_2$ receptor. It is accordingly believed that compounds which can interact selectively with the 5-HT$_{2A}$ receptor relative to the dopamine D$_2$ receptor will display the beneficial level of antipsychotic activity associated with 5-HT$_{2A}$ receptor antagonism, whilst minimizing or even avoiding the extrapyramidal and other side-effects arising from an interaction with dopamine D$_2$ receptors.

The compounds of the present invention are potent antagonists of the human 5-HT$_{2A}$ receptor, and are accordingly of benefit in the treatment and/or prevention of psychotic disorders such as schizophrenia. The compounds of the invention may display more effective binding to the human 5-HT$_{2A}$ receptor than to the human dopamine D$_2$ receptor, and they can therefore be expected to manifest fewer side-effects than compounds which do not discriminate in their binding affinity as between 5-HT$_{2A}$ and D$_2$ receptors.

By virtue of their potent human 5-HT$_{2A}$ receptor antagonist activity; the compounds of the present invention are also effective in the treatment, of neurological conditions including depression, anxiety, panic disorder, obsessive-compulsive disorder, pain, sleep disorders such as insomnia, eating disorders such as anorexia nervosa, and dependency or acute toxicity associated with narcotic agents such as LSD or MDMA; and moreover are beneficial in controlling the extrapyramidal symptoms associated with the administration of neuroleptic agents. They may further be effective in the lowering of intraocular pressure and may therefore be beneficial in treating glaucoma (cf. T. Mano et al. and H. Takaneka et al., *Investigative Ophthalmitology and Visual Scienice,* 1995, vol. 36, pages 719 and 734 respectively).

Being 5-HT$_{2A}$ receptor antagonists, the compounds of the present invention may also be beneficial in preventing or reducing the toxic symptoms associated with the intake of ergovaline in animals consuming *Acremonium coenophialum* infected tall fescue (cf. D. C. Dyer, *Life Sciences,* 1993, 53, 223–228).

Various classes of compounds containing inter alia a sulphonyl moiety, which are stated to have activity as antipsychotic agents, are described in WO 96/35666, EP-A-0261688, and U.S. Pat. Nos. 4,218,455 and 4,128,552. A further series of compounds, containing inter alia a piperidinyl-sulphonyl-indole moiety, is described in U.S. Pat. No. 5,418,242, and alleged to possess analgesic properties. DE-A-3901735 relates to the use of a class of compounds containing inter alia a sulphonylpyridine moiety in the treatment of depression. None of these publications, however, discloses or suggests the particular class of phenylsulphonyl derivatives provided by the present invention.

The compounds according to the present invention are potent and selective 5-HT$_{2A}$ receptor antagonists having a human 5-HT$_{2A}$ receptor binding affinity (K$_i$) of 100 nM or less, typically of 50 nM or less and preferably of 10 nM or less. The compounds of the invention may possess at least a 10-fold selective affinity, suitably at least a 20-fold selective affinity and preferably at least a 50-fold selective affinity, for the human 5-HT$_{2A}$ receptor relative to the human dopamine D$_2$ receptor.

The present invention provides a compound of formula I, or a salt thereof:

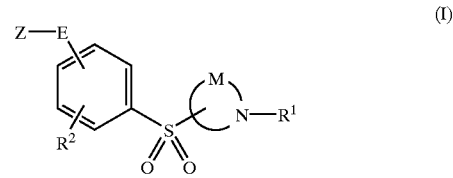

wherein

Z represents hydrogen, halogen, cyano, nitro, trifluoromethyl, trifluoromethoxy, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$ or —CONR$^a$R$^b$; or Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole; or Z represents an optionally substituted six-membered heteroaromatic ring selected from pyridine, pyrazine, pyrimidine and pyridazine;

R$^a$ and R$^b$ independently represent hydrogen or C$_{1-6}$ alkyl; or R$^a$ and R$^b$, when linked through a nitrogen atom, together represent the residue of an azetidine, pyrrolidine, piperidine or morpholine ring;

E represents a chemical bond or a straight or branched alkylene chain containing from 1 to 4 carbon atoms, optionally incorporating an oxygen atom to form an ether linkage;

M represents the residue of an azetidine, pyrrolidine or piperidine ring;

$R^1$ represents an optionally substituted aryl($C_{2-4}$)alkyl group; and $R^2$ represents hydrogen or halogen.

Where Z in the compounds of formula I above represents a five-membered heteroaromatic ring, this ring may be optionally substituted by one or, where possible, two substituents. As will be appreciated, where $Z_i$ represents an oxadiazole, thiadiazole or tetrazole ring, only one substituent will be possible; otherwise, one or two optional substituents may be accommodated around the five-membered heteroaromatic ring Z.

Where Z in the compounds of formula I above represents a six-membered heteroaromatic ring, this ring may be optionally substituted by one or more substituents, typically by one or two substituents.

Examples of suitable substituents on the five-membered or six-membered heteroaromatic ring as specified for Z include halogen, cyano, trifluoromethyl, $C_{1-6}$ alkyl, $C_{1-6}$ alkoxy, $C_{1-6}$ alkylthio, amino, $C_{1-6}$ alkylamino and di($C_{1-6}$)alkylamino, especially methyl.

The aryl($C_{2-4}$)alkyl group $R^1$ may be optionally substituted by one or more substituents. Suitably, the aryl($C_{2-4}$)alkyl group $R^1$ is unsubstituted, or substituted by one, two or three substituents. More particularly, the aryl($C_{2-4}$)alkyl group $R^1$ may be unsubstituted, or substituted by one or two substituents. Any optional substitution on the aryl($C_{2-4}$)alkyl group $R^1$ will suitably be on the aryl moiety thereof, although substitution on the alkyl moiety thereof is an alternative possibility.

Representative examples of optional substituents on the group $R^1$ include halogen, nitro, trifluoromethyl, trifluoromethoxy, $C_{1-6}$ alkyl, keto, hydroxy, $C_{1-6}$ alkoxy, $C_{1-6}$ alkylthio or di($C_{1-6}$)alkylamino.

Illustrative examples of optional substituents on the group $R^1$ include halogen, nitro, trifluoromethyl, trifluoromethoxy, $C_{1-6}$ alkyl, hydroxy, $C_{1-6}$ alkoxy, $C_{1-6}$ alkylthio or di($C_{1-6}$) alkylamino.

As used herein, the expression "$C_{1-6}$ alkyl" includes methyl and ethyl groups, and straight-chained or branched propyl, butyl, pentyl and hexyl groups. Particular alkyl groups are methyl, ethyl, n-propyl, isopropyl and tert-butyl. Derived expressions such as "$C_{1-6}$ alkoxy", "$C_{1-6}$ alkylthio" and "$C_{1-6}$ alkylamino" are to be construed accordingly.

Typical aryl groups include phenyl and naphthyl, preferably phenyl.

The expression "aryl($C_{2-4}$)alkyl" as used herein includes phenylethyl, phenylpropyl and naphthylethyl, especially phenylethyl.

The term "halogen" as used herein includes fluorine, chlorine, bromine and iodine, especially fluorine or chlorine.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Typically, the substituent Z in the compounds of formula I above represents hydrogen, halogen, cyano, —$NR^aCOR^b$, —$CO_2R^a$ or —$CONR^aR^b$; or an optionally substituted five-membered ring as specified above.

Suitably, the substituent Z represents hydrogen, cyano, —$NR^aCOR^b$ or —$CONR^aR^b$; or an optionally substituted five-membered ring as specified above.

Suitably, $R^a$ represents hydrogen or methyl, especially hydrogen.

Suitably, $R^b$ represents hydrogen or methyl, especially hydrogen.

Where the group Z represents an optionally substituted five-membered heteroaromatic ring, this is suitably an imidazole, pyrazole, 1,2,3-triazole, 1,2,4-triazole or tetrazole ring, any of which may be optionally substituted, typically by methyl.

Specific values for the group Z include hydrogen, bromo, cyano, acetylamino, methoxycarbonyl, carboxamido, imidazol-1-yl, pyrazol-1-yl, 1,2,3-triazol-1-yl, 1,2,4-triazol-1-yl, 1-methyl-1,2,4-triazol-5-yl, tetrazol-1-yl and 2-methyltetrazol-5-yl.

Particular values for the group Z include hydrogen, cyano, acetylamino, carboxamido, imidazol-1-yl, pyrazol-1-yl, 1,2, 3-triazol-1-yl, 1,2,4-triazol-1-yl, 1-methyl-1,2,4-triazol-5-yl, tetrazol-1-yl and 2-methyltetrazol-5-yl.

One specific value of Z is carboxamido.

Another specific value of Z is cyano.

Where E represents a straight or branched alkylene chain, this may be, for example, methylene, ethylene, 1-methylethylene, propylene, 2-methylpropylene or butylene. The alkylene chain E may optionally incoporate an oxygen atom, thereby forming an ether linkage. Moreover, E may represent a chemical bond such that the moiety Z is attached directly to the phenyl ring as depicted in formula I above.

Preferably, E represents a chemical bond or a methylene linkage.

In a specific embodiment, E represents a chemical bond.

In one particular configuration, the moiety Z—E— in the compounds of formula I is attached at the para position relative to the sulphonyl group, in which case the present invention suitably provides a compound of formula IA, or a salt thereof:

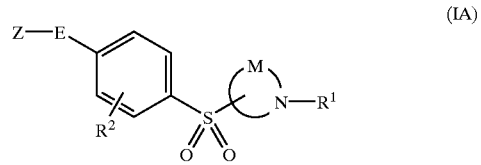

(IA)

wherein Z, E, M, $R^1$ and $R^2$ are as defined above.

The moiety M preferably represents the residue of a piperidine ring, in which case the present invention suitably provides a compound of formula IB, or a salt thereof:

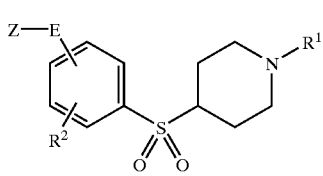

(IB)

wherein Z, E, $R^1$ and $R^2$ are as defined above.

Suitably, $R^1$ represents optionally substituted phenylethyl or optionally substituted phenylpropyl. In addition, $R^1$ may represent optionally substituted naphthylethyl.

Preferably, $R^1$ represents phenylethyl, which may be unsubstituted, or substituted by one or more substituents. Typically, the phenylethyl group $R^1$ will be unsubstituted, or substituted by one, two or three (especially one or two) substituents. In a particular embodiment, $R^1$ represents disubstituted phenylethyl.

Examples of specific substituents on the group $R^1$ include fluoro, chloro, bromo, iodo, nitro, trifluoromethyl, methyl, keto, hydroxy, methoxy, methylthio and dimethylamino.

Particular examples of optional substituents on $R^1$ include fluoro, chloro, bromo, iodo, nitro, trifluoromethyl, methyl, hydroxy, methoxy, methylthio and dimethylamino.

Specific examples of optional substituents on $R^1$ include fluoro, chloro and keto, especially fluoro.

Representative values of $R^1$ include phenylethyl, fluoro-phenylethyl, chloro-phenylethyl, bromo-phenylethyl, iodo-phenylethyl, difluoro-phenylethyl, dichloro-phenylethyl, (chloro)(fluoro)-phenylethyl, (fluoro)-(trifluoromethyl)-phenylethyl, (bromo)(methoxy)-phenylethyl, trifluoro-phenylethyl, nitro-phenylethyl, methyl-phenylethyl, hydroxy-phenylethyl, methoxy-phenylethyl, dimethoxy-phenylethyl, (hydroxy)(methoxy)-phenylethyl, (hydroxy)(dimethoxy)-phenylethyl, trimethoxy-phenylethyl, methylthio-phenylethyl, dimethylamino-phenylethyl, phenylpropyl, hydroxy-phenylpropyl and naphthylethyl. Additional values of $R^1$ include fluorophenyl-oxoethyl and chlorophenyl-oxoethyl.

Typical values of $R^1$ include phenylethyl, fluoro-phenylethyl, chloro-phenylethyl, difluoro-phenylethyl, fluorophenyl-oxoethyl and chlorophenyl-oxoethyl.

Particular values of $R^1$ include phenylethyl, fluoro-phenylethyl, chloro-phenylethyl and difluoro-phenylethyl.

Suitably, $R^1$ may represent 2-phenylethyl, 2-fluoro-2-phenylethyl, 2-(4-fluorophenyl)ethyl, 2-(2-chlorophenyl)ethyl, 2-(2,4-difluorophenyl)ethyl, 2-(4-fluorophenyl)-2-oxoethyl or 2-(4-chlorophenyl)-2-oxoethyl.

One specific value of $R^1$ is 2-(2,4-difluorophenyl)ethyl.

Another specific value of $R^1$ is 2-(4-fluorophenyl)-2-oxoethyl.

Suitably, $R^2$ represents hydrogen or fluoro, especially hydrogen.

A particular sub-class of compounds according to the invention is represented by the compounds of formula IIA, and salts thereof:

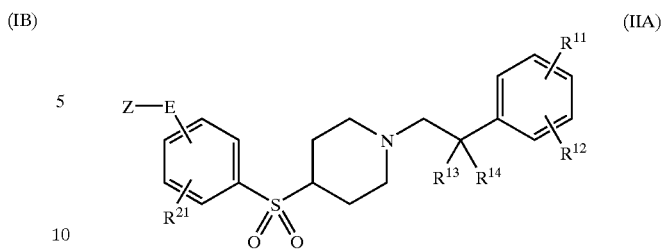

(IIA)

wherein
Z and E are as defined with reference to formula I above;
$R^{11}$ and $R^{12}$ independently represent hydrogen, halogen, nitro, trifluoromethyl, $C_{1-6}$ alkyl, hydroxy, $C_{1-6}$ alkoxy, $C_{1-6}$ alkylthio or di($C_{1-6}$)alkylamino;
$R^{13}$ represents hydrogen and $R^{14}$ represents hydrogen or fluoro, or $R^{13}$ and $R^{14}$ together represent keto; and
$R^{21}$ represents hydrogen or fluoro.

Suitably, $R^{11}$ represents hydrogen, fluoro, chloro or methoxy, especially hydrogen or fluoro.

Suitably, $R^{12}$ represents hydrogen, fluoro, chloro, bromo, iodo, nitro, trifluoromethyl, methyl, hydroxy, methoxy, methylthio or dimethylamino. More particularly, $R^{12}$ may represent hydrogen, fluoro or chloro.

In one embodiment of the compounds of formula IIA above, $R^{13}$ represents hydrogen and $R^{14}$ represents hydrogen or fluoro.

In another embodiment of the compounds of formula IIA, $R^{13}$ and $R^{14}$ together represent keto.

Suitably, $R^{13}$ and $R^{14}$ are both hydrogen.

Suitably, $R^{21}$ is hydrogen.

Another sub-class of compounds according to the invention is represented by the compounds of formula IIB, and salts thereof:

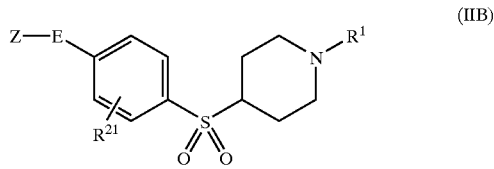

(IIB)

wherein
Z, E and $R^1$ are as defined with reference to formula I above; and
$R^{21}$ is as defined with reference to formula IIA above.

A particular subset of the compounds of formula IIA and IIB above is represented by the compounds of formula IIC, and salts thereof:

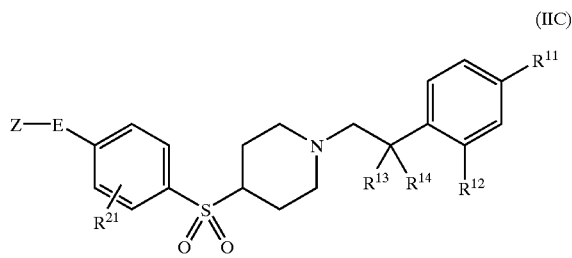

(IIC)

wherein Z, E, $R^{11}$, $R^{12}$, $R^{13}$, $R^{14}$ and $R^{21}$ are as defined above.

In one embodiment of the compounds of formula IIC above, $R^{13}$ and $R^{14}$ are both hydrogen.

Specific compounds within the scope of the present invention include:

4-(4-cyanophenylsulphonyl)-1-[2-(2,4-difluorophenyl)ethyl]piperidine;
4-(4-acetylaminophenylsulphonyl)-1-[2-(2,4-difluorophenyl)ethyl]-piperidine;
4-(4-cyano-3-fluorophenylsulphonyl)-1-[2-(2,4-difluorophenyl)ethyl]-piperidine;
1-[2-(2,4-difluorophenyl)ethyl]-4-[4-(1,2,4-triazol-1-yl)phenylsulphonyl]-piperidine;
1-[2-(2,4-difluorophenyl)ethyl]-4-[4-(imidazol-1-yl)phenylsulphonyl]-piperidine;
1-[2-(2,4-difluorophenyl)ethyl]-4-[4-(pyrazol-1-yl)phenylsulphonyl]-piperidine;
1-[2-(2,4-difluorophenyl)ethyl]-4-[4-(1,2,3-triazol-1-yl)phenylsulphonyl]-piperidine;
4-(4-carboxamidophenylsulphonyl)-1-[2-(2,4-difluorophenyl)ethyl]-piperidine;
4-(4-carboxamido-3-fluorophenylsulphonyl)-1-[2-(2,4-difluorophenyl)ethyl]-piperidine;
1-[2-(2,4-difluorophenyl)ethyl]-4-[4-(2-methyltetrazol-5-yl)-phenylsulphonyl]piperidine;
1-[2-(2,4-difluorophenyl)ethyl]-4-[4-(1-methyl-1,2,4-triazol-5-yl)-phenylsulphonyl]piperidine;
1-[2-(2,4-difluorophenyl)ethyl]-4-[4-(tetrazol-1-ylmethyl)phenylsulphonyl]-piperidine;
4-(4-carboxamidophenylsulphonyl)-1-(2-phenylethyl)piperidine;
4-(4-carboxamidophenylsulphonyl)-1-[2-(4-fluorophenyl)ethyl]piperidine;
4-(4-carboxamidophenylsulphonyl)-1-[2-(2-chlorophenyl)ethyl]piperidine;
4-(4-carboxamidophenylsulphonyl)-1-(2-fluoro-2-phenylethyl)piperidine;
1-[2-(2,4-difluorophenyl)ethyl]-4-phenylsulphonylpiperidine;
4-(3-carboxamidophenylsulphonyl)-1-[2-(2,4-difluorophenyl)ethyl]-piperidine;
4-(4-bromophenylsulphonyl)-1-[2-(4-fluorophenyl)-2-oxoethyl]piperidine;
4-(4-cyanophenylsulphonyl)-1-[2-(4-fluorophenyl)-2-oxoethyl]piperidine;
1-[2-(4-fluorophenyl)-2-oxoethyl]-4-phenylsulphonylpiperidine;
1-[2-(4-chlorophenyl)-2-oxoethyl]-4-phenylsulphonylpiperldine;

and salts thereof.

The invention also provides pharmaceutical compositions comprising one or more of the compounds according to this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Favoured unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric. acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

If desired, the compounds according to this invention may be co-administered with another anti-schizophrenic medicament, for example one producing its effects via dopamine $D_2$ and/or $D_4$ receptor subtype blockade. In such circumstances, an enhanced anti-schizophrenic effect may be envisaged without a corresponding increase in side-effects such as those caused by, for example, $D_2$ receptor subtype blockade; or a comparable anti-schizophrenic effect with reduced side-effects may alternatively be envisaged. Such co-administration may be desirable where a patient is already established on an anti-schizophrenic treatment regime involving conventional anti-schizophrenic medicaments. Suitable anti-schizophrenic medicaments of use in combination with the compounds according to the present invention include haloperidol, chlorpromazine, mesoridazine, thioridazine, acetophenazine, fluphenazine, perphenazine, trifluoperazine, chloroprothixene, thiothixene, clozapine, olanzapine, pimozide, molindone, loxapine, sulpiride, risperidone, xanomeline, fananserin and ziprasidone, and pharmaceutically acceptable salts thereof.

The compounds according to the present invention may be prepared by a process which comprises attachment of the $R^1$ moiety to a compound of formula III:

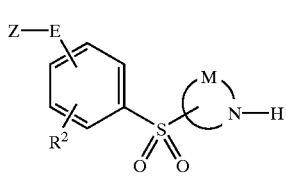

(III)

wherein Z, E, M and $R^2$ are as defined above; by conventional means including N-alkylation.

Attachment of the $R^1$ moiety to the compounds of formula III may conveniently be effected by standard alkylation techniques. One example thereof comprises treatment with an aryl($C_{2-4}$)alkyl halide, especially a bromide derivative $R^1$—Br such as 2-phenylethyl bromide or 2-(2,4-difluorophenyl)ethyl bromide, typically under basic conditions, e.g. potassium carbonate or caesium carbonate, in a solvent such as acetonitrile or N,N-dimethylformamide, suitably at an elevated temperature and optionally in the presence of sodium iodide. Another example comprises treatment of the compound of formula III with an aryl($C_{2-4}$)alkyl mesylate $R^1$—$OSO_2CH_3$ such as 2-phenylethyl methanesulphonate, typically in the presence of sodium carbonate and sodium iodide, in a suitable solvent such as 1,2-dimethoxyethane.

Alternatively, the $R^1$ moiety may conveniently be attached by reductive alkylation, which may be accomplished in a single step, or as a two-step procedure. The single-step approach, for the preparation of a compound of formula I wherein $R^1$ corresponds to a group of formula —$CH_2R^{1a}$, suitably comprises treating the required compound of formula III as defined above with the appropriate aldehyde of formula $R^{1a}$—CHO, e.g. phenylacetaldehyde, in the presence of a reducing agent such as sodium cyanoborohydride. In a typical two-step procedure, a carboxylic acid derivative of formula $R^{1a}$—$CO_2H$ is condensed with the required compound of formula III, suitably in the presence of a condensing agent such as (i) bis(2-oxo-3-oxazolidinyl)phosphinic chloride and triethylamine, or (ii) 1-(3-dimethylaminopropyl)-3-ethylcarbodiimide hydrochloride and 1-hydroxybenzotriazole hydrate, to afford a compound corresponding to formula I wherein $R^1$ represents —$COR^{1a}$; the carbonyl group thereof can then be reduced, for example by treatment with borane-tetrahydrofuran complex, or with dilsobutylaluminium hydride, and the required compound of formula I thereby obtained.

The compounds of formula III above may be prepared by oxidation of the corresponding compound of formula IV:

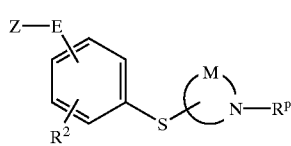

(IV)

wherein Z, E, M and $R^2$ are as defined above, and $R^p$ represents an amino-protecting group; with subsequent removal of the amino-protecting group $R^p$.

The amino-protecting group $R^p$ in the compounds of formula IV is suitably a carbamoyl moiety such as tert-butoxycarbonyl (BOC), which can readily be removed as required by treatment under acidic conditions, e.g. in refluxing methanolic hydrochloric acid.

Similarly, the compounds according to the invention may be prepared by a process which comprises oxidizing a compound of formula V:

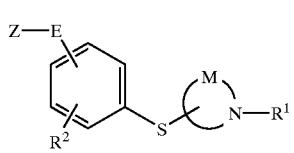

(V)

wherein Z, E, M, $R^1$ and $R^2$ are as defined above.

Oxidation of the compounds of formula IV or V may conveniently be accomplished by treating the appropriate substrate with an oxidizing agent. Typical oxidizing agents of use in this transformation include meta-chloroperbenzoic acid and Oxone®. In an alternative procedure, compound IV or V may be oxidized by treatment with ruthenium(IV) oxide and sodium periodate in a suitable solvent which may typically comprise a mixture of carbon tetrachloride and aqueous acetonitrile.

The intermediates of formula IV and V may be prepared by reacting a compound of formula VI with a compound of formula VII:

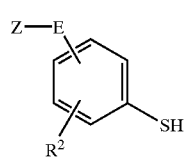

(VI)

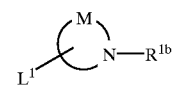

(VII)

wherein Z, E, M and $R^2$ are as defined above, $R^{1b}$ represents an amino-protecting group $R^p$ or corresponds to the moiety $R^1$ as defined above, and $L^1$ represents a suitable leaving group.

The leaving group $L^1$ in the compounds of formula VII above suitably represents a $C_{1-4}$ alkylsulphonyloxy group such as methanesulphonate (mesylate), in which case the desired intermediate of formula VII can be prepared from the corresponding precursor compound of formula VII wherein LI represents hydroxy by mesylation under standard conditions.

The reaction between compounds VI and VII is conveniently effected in a solvent such as acetonitrile, generally in the presence of a base such as potassium carbonate, suitably at an elevated temperature which might typically be the reflux temperature of the solvent employed.

Where they are not commercially available, the starting materials of formula VI may be prepared by procedures analogous to those described in the accompanying Examples, or by standard methods well known from the art.

It will be appreciated that any compound of formula I initially obtained from any of the above processes may, where appropriate, subsequently be elaborated into a further desired compound of formula I using techniques known from the art. For example, a compound of formula I initially obtained wherein the moiety Z—E— represents bromo may be converted into the corresponding compound of formula I wherein the moiety Z—E— represents cyano by treatment with copper(I) cyanide in the presence of 1-methyl-2-pyrrolidinone (NMP), or with zinc cyanide in the presence of tetrakis(triphenylphosphine)palladium(O). The resulting compound of formula I wherein the moiety Z—E— represents cyano thereby obtained may in turn be converted into the corresponding compound of formula I wherein the moiety Z—E— represents carboxamido by heating in mineral acid, e.g. 85% sulphuric acid at 100° C., or by treatment with potassium trimethylsilanolate, typically in tetrahydrofuran at reflux. Alternatively, a compound of formula I initially obtained wherein the moiety Z—E— represents bromo may be converted directly into the corresponding compound of formula I wherein the moiety Z—E— represents carboxamido by heating under a carbon monoxide atmosphere in the presence of 1,1,1,3,3,3-hexamethyldisilazane, dilsopropylamine, palladium(II) acetate and 1,3-bis(diphenylphosphino)propane. Where, for example, the moiety Z—E— in the compounds of formula I represents an optionally substituted N-linked pyrrole, imidazole, pyrazole, triazole or tetrazole moiety, e.g. imidazol-1-yl, pyrazol-1-yl, 1,2,3-triazol-1-yl or 1,2,4-triazol-1-yl, these compounds may be prepared by treating the corresponding compound of formula I wherein Z—E— represents bromo with the appropriate optionally substituted pyrrole, imidazole, pyrazole, triazole or tetrazole derivative, in the presence of copper bronze and sodium hydride, typically with heating in NMP. Where, for example, the moiety Z—E— in the compounds of formula I represents an optionally substituted C-linked five-membered heteroaromatic ring, e.g. 2-methyltetrazol-5-yl or 1-methyl-1,2,4-triazol-5-yl, these compounds may be prepared by reacting the corresponding compound of formula I wherein Z—E— represents bromo with a tributylstannyl derivative of the appropriate heteroaromatic compound, e.g. 2-methyl-5-tributylstannyltetrazole or 1-methyl-5-tributylstannyl-1,2,4-triazole, in the presence of a transition metal catalyst such as tetrakis(triphenylphosphine)palladium(O), typically with heating in a solvent such as N,N-dimethylformamide. A compound of formula I wherein, for example, Z represents a tetrazol-1-yl moiety and E is methylene may be prepared from the corresponding compound of formula I wherein the moiety Z—E— represents hydroxymethyl, by mesylation under standard conditions followed by displacement of the mesyl group by treatment with tetrazole, typically in the presence of sodium iodide and a base such as caesium carbonate; the compound of formula I wherein Z—E— represents hydroxymethyl may suitably be prepared by diisobutylaluminium hydride (DIBAL-H) reduction of the corresponding compound of formula I wherein Z—E— represents a $C_{2-6}$ alkoxycarbonyl group, e.g. methoxycarbonyl, which in turn may be prepared by treatment of the corresponding compound of formula I wherein Z—E— represents bromo with 1,1'-bis(diphenylphosphino) ferrocene; palladium(II) acetate, triethylamine and a $C_{1-6}$ alkanol such as methanol, in an atmosphere of carbon monoxide. A compound of formula I wherein Z—E— represents $C_{2-6}$ alkoxycarbonyl, e.g. methoxycarbonyl, may be converted to the corresponding compound of formula I wherein Z—E— represents carboxamido by treatment with ammonium chloride in the presence of trimethylaluminium.

Where the above-described processes for the preparation of the compounds of use in the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-l-tartaric acid, followed by fractional crystallization and regeneration of the free base. The compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent, stage using methods known from the art.

The following Examples illustrate the preparation of compounds of use in the invention.

The compounds in accordance with this invention potently inhibit [$^3$H]-ketanserin binding to the human 5-HT$_{2A}$ receptor expressed in clonal cell lines. Moreover, those compounds of the invention which have been tested display a selective affinity for the 5-HT$_{2A}$ receptor relative to the dopamine D$_2$ receptor.

The compounds of the accompanying Examples were all found to possess a $K_i$ value for displacement of [$^3$H]-ketanserin from the human 5-HT$_{2A}$ receptor, when expressed in Chinese hamster ovary (CHO) clonal cell lines, of 100 nM or less.

EXAMPLE 1

4-(4-Cyanophenylsulphonyl)-1-[2-(2,4-difluorophenyl)ethyl]piperidine a) N-BOC 4-mesyloxypiperidine A solution of methanesulphonyl chloride (20 ml, 0.26 mol) in CH$_2$Cl$_2$ (200 ml) was added dropwise over 15 min to a solution of N-BOC 4-piperidinol (46 g, 0.23 mol) and Et$_3$N (64 ml, 0.46 mol) in CH$_2$Cl$_2$ (430 ml) cooled below 7° C. using a salt/ice bath. After addition was complete, stirring was continued for 15 min. The reaction was warmed to room temperature and quenched with 1N HCl (200 ml). The organic phase was washed with further 1N HCl (200 ml), brine (50 ml), 1N NaOH (100 ml), dried (MgSO$_4$) and evaporated to give 60 g (94% yield) of product as a colourless solid. $\delta_H$ (360 MHz, CDCl$_3$) 1.46 (9H, s), 1.75–1.85 (2H, m), 1.90–2.00 (2H, m), 3.0 (3H, s), 3.25–3.35 (2H, m), 3.65–3.75 (2H, m), 4.85–4.95 (1H, m).

b) N-BOC 4-(4-bromophenylthio)piperidine

N-BOC 4-mesyloxypiperidine (40 g, 0.14 mol), 4-bromothiophenol (32 g, 0.17 mol) and potassium carbonate (30 g, 0.22 mol) were mixed at room temperature in CH$_3$CN (300 ml) and heated at reflux for 18 h. Work-up by partitioning between water and EtOAc afforded 50 g of material as a yellow oil. $\delta_H$ (360 MHz, CDCl$_3$) 1.44 (9H, s), 1.45–1.55 (2H, m), 1.85–1.95 (2H, m), 2.85–2.95 (2H, m), 3.10–3.20 (1H, m), 3.95–4.05 (2H, m), 7.25–7.30 (2H, m), 7.40–7.45 (2H, m).

c) N-BOC 4-(4-bromophenylsulphonyl)piperidine

Water (26 ml) was added to alumina (130 g) which was slurried (5 min) and chloroform (500 ml) added followed by a solution of N-BOC 4-(4-bromophenylthio)piperidine (50 g, 0.13 mol) in chloroform (300 ml). Oxone (250 g, 0.39 mol) was added and the resulting slurry stirred and heated at reflux for 18 h. After cooling to room temperature the mixture was filtered and the mother liquor washed with water, dried (MgSO$_4$) and evaporated to give the product as a colourless solid. $\delta_H$ (360 MHz, CDCl$_3$) 1.43 (9H, s), 1.50–1.70 (2H, m), 1.90–2.00 (2H, m), 2.55–2.70 (2H, m), 2.90–3.10 (1H, m), 4.15–4.25 (2H, m), 7.73 (4H, s).

d) 4-(4-Bromophenylsulphonyl)piperidine

N-BOC 4-(4-bromophenylsulphonyl)piperidine (63 g, 0.156 mol) was dissolved in methanol (300 ml) and 5N HCl (63 ml) and heated at reflux for 3 h. After a warm filtration to remove insolubles the solution was cooled to afford crystalline HCl salt (15.4 g) which was collected by filtration. Neutralisation of the mother liquor with sodium carbonate and extraction with CH$_2$Cl$_2$ afforded 16 g of additional material, a colourless solid, as the free base. Hydrochloride: $\delta_H$ (400 MHz, DMSO-d$_6$) 1.65–1.80 (2H, m), 1.95–2.05 (2H, m), 1.80–2.90 (2H, m), 3.25–3.35 (2H, m), 3.60–3.70 (1H, m), 7.80 (2H, d, J 8 Hz), 7.90 (2H, d, J 8 Hz). Free base: $\delta_H$ (360 MHz, CDCl$_3$) 1.45–1.60 (2H, m), 1.95–2.00 (2H, m), 2.50–2.60 (2H, m), 2.95–3.05 (1H, m), 3.15–3.25 (2H, m), 7.70 (4H, s).

e) 4-(4-Bromophenylsulphonyl)-1-[2-(2,4-difluorophenyl)ethyl]piperidine

A mixture of 4-(4-bromophenylsulphonyl)piperidine (7.6 g, 0.025 mol), 2,4-difluorophenethyl bromide (8.3 g, 0.38 mol), potassium carbonate (7.5 g, 0.054 mol) and sodium iodide (5.6 g, 0.037 mol) in CH$_3$CN (70 ml) was heated at reflux under nitrogen for 18 h. The reaction mixture was then concentrated and partitioned between water and EtOAc. The organic phase was washed with brine, dried (Na$_2$SO$_4$) and concentrated. Trituration with hexane gave 6.5 g of product as a colourless solid. $\delta_H$ (360 MHz, CDCl$_3$) 1.55–1.75 (2H, m), 1.95–2.05 (4H, m), 2.45–2.55 (2H, m), 2.70–2.75 (2H, m), 2.85–2.95 (1H, m), 3.05–3.10 (2H, m), 6.70–6.85 (2H, m), 7.10–7.15 (1H, m), 7.72 (4H, s).

f) 4-(4-Cyanophenylsulphonyl)-1-[2-(2,4-difluorophenyl)ethyl]piperidine

A mixture of 4-(4-bromophenylsulphonyl)-1-[2-(2,4-difluorophenyl)ethyl]piperidine (2.2 g, 4.9 mmol) and copper(I) cyanide (2.3 g, 25 mmol) in NMP (3 ml) was heated under nitrogen at 160° C. for 16 h while stirring. The hot solution was poured into water/CH$_2$Cl$_2$ (100/200 ml), the organic phase was washed with water, dried (Na$_2$SO$_4$) and evaporated to yield a syrup. Column chromatography [silica, petrol/ethyl acetate (1:1)] followed by recrystallisation from ethyl acetate yielded 1.05 g of crystalline material. $\delta_H$ (360 MHz, CDCl$_3$) 1.56–1.76 (2H, m), 1.97–2.04 (4H, m), 2.50–2.54 (2H, m), 2.71–2.75 (2H, m), 2.90–2.97 (1H, m), 3.05–3.10 (2H, m), 6.72–6.80 (2H, m), 7.08–7.12 (1H, m), 7.87–7.89 (2H, m), 7.99–8.02 (2H, m).

Following Example 1 Steps a–e, using the appropriate thiophenol in Step b, the following Examples were prepared:

EXAMPLE 2

4-(4-Acetylaminophenylsulphonyl)-1-[2-(2,4-difluorophenyl)ethyl]piperidine $\delta_H$ (360 MHz, CDCl$_3$) 1.55–1.78 (2H, m), 1.96–2.05 (4H, m), 2.22 (3H, s), 2.49–2.52 (2H, m), 2.71–2.75 (2H, m), 2.84–2.92 (1H, m), 3.03–3.08 (2H, m), 6.71–6.80 (2H, m), 7.08–7.15 (1H, m), 7.70–7.79 (4H, m), 7.89 (1H, s).

EXAMPLE 3

4-(4-Cyano-3-fluorophenylsulphonyl)-1-[2-(2,4-difluorophenyl)ethyl]piperidine $\delta_H$ (400 MHz, CDCl$_3$) 1.68–1.79 (2H, m), 1.98–2.04 (4H, m), 2.51–2.55 (2H, m), 2.71–2.75 (2H, m), 2.91–2.99 (1H, m), 3.06–3.09 (2H, m), 6.73–6.81 (2H, m), 7.09–7.14 (1H, m), 7.75–7.81 (2H, m), 7.85–7.89 (1H, m).

EXAMPLE 4

1-[2-(2,4-Difluorophenyl)ethyl]-4-[4-(1,2,4-triazol-1-yl)phenylsulphonyl]piperidine A mixture of 1,2,4-triazole (0.175 g, 2.5 mmol), 4-(4-bromophenylsulphonyl)-1-[2-(2,4-difluorophenyl)ethyl]piperidine (0.54 g, 1.2 mmol), copper bronze (80 mg) and sodium hydride (60%, 100 mg, 2.5 mmol) in NMP (3 ml) was heated under nitrogen at 160° C. for 16 h while stirring. The hot solution was poured into water/CH$_2$Cl$_2$ (10/20 ml) and further extracted into CH$_2$Cl$_2$. The combined organic phase was washed with water, dried (Na$_2$SO$_4$) and evaporated to yield a syrup. Column chromatography [silica, hexane/EtOAc (1:1)] yielded 250 mg of crystalline material. $\delta_H$ (360 MHz, CDCl$_3$) 1.68–1.79 (2H, m), 1.98–2.05 (4H, m), 2.50–2.54 (2H, m), 2.71–2.75 (2H, m), 2.90–2.99 (1H, m), 3.05–3.09 (2H, m), 6.72–6.81 (2H, m), 7.09–7.15 (1H, m), 7.93–8.04 (4H, m), 8.17 (1H, s), 8.72 (1H, s).

Following Example 4, using the appropriate heterocycle, the following Examples were prepared:

EXAMPLE 5

1-[2-(2,4-Difluorophenyl)ethyl]-4-[4-(imidazol-1-yl)phenylsulphonyl]piperidine $\delta_H$ (360 MHz, CDCl$_3$) 1.66–1.80 (2H, m), 1.94–2.12 (4H, m), 2.46–2.58 (2H, m), 2.66–2.78 (2H, m), 2.88–2.98 (1H, m), 3.02–3.14 (2H, m), 6.68–6.84 (2H, m), 7.06–7.18 (1H, m), 7.33–7.40 (1H, s), 7.56–7.64 (2H, m), 7.92–8.06 (4H, m).

EXAMPLE 6

1-[2-(2,4-Difluorophenyl)ethyl]-4-[4-(pyrazol-1-yl)phenylsulphonyl]piperidine $\delta_H$ (360 MHz, CDCl$_3$) 1.67–1.82 (2H, m), 1.93–2.09 (4H, m), 2.46–2.57 (2H, m), 2.67–2.78 (2H, m), 2.86–2.98 (1H, m), 3.02–3.12 (2H, m), 6.52–6.58 (1H, s), 6.68–6.82 (2H, m), 7.06–7.18 (1H, m), 7.76–7.82 (1H, s), 7.86–7.98 (4H, m), 7.98–8.06 (1H, s).

EXAMPLE 7

1-[2-(2,4-Difluorophenyl)ethyl]-4-[4-(1,2,3-triazol-1-yl)phenylsulphonyl]piperidine $\delta_H$ (360 MHz, CDCl$_3$) 1.66–1.82 (2H, m), 1.94–2.10 (4H, m), 2.48–2.56 (2H, m), 2.69–2.77 (2H, m), 2.89–3.02 (1H, m), 3.02–3.12 (2H, m), 6.69–6.83 (2H, m), 7.06–7.16 (1H, m), 7.86–7.94 (1H, s), 7.94–8.07 (4H, m), 8.07–8.12 (1H, m).

EXAMPLE 8

4-(4-Carboxamidophenylsulphonyl)-1-[2-(2,4-difluorophenyl)ethyl]piperidine

A solution of 4-(4-cyanophenylsulphonyl)-1-[2-(2,4-difluorophenyl)ethyl]piperidine (0.5 g, 1.28 mmol) (Example 1) in 85% H$_2$SO$_4$ (10 ml) was heated at 100° C. for 30 min. The cooled solution was diluted with water (40 ml) and neutralized with solid KOH. At pH 7 a precipitate was collected and dissolved in CH$_2$Cl$_2$. The organic phase was dried (MgSO$_4$) and concentrated to yield the title compound, m.p. 195–197° C. (softens 186–189° C.). $\delta_H$ (360 MHz, CDCl$_3$) 1.70–1.77 (2H, m), 1.97–2.03 (4H, m), 2.50–2.54 (2H, m), 2.71–2.75 (2H, m), 2.89–2.92 (1H, m), 3.04–3.07 (2H, m), 5.74 (1H, s), 6.15 (1H, s), 6.73–6.80 (2H, m), 7.08–7.12 (1H, m), 7.94–8.00 (4H, s).

EXAMPLE 9

4-(4-Carboxamido-3-fluorolphenylsulphonyl)-1-[2-(2,4-difluorophenyl)ethyl]piperidine A mixture of 4-(4-cyano-3-fluorophenylsulphonyl)-1-[2-(2,4-difluorophenyl)ethyl]piperidine (0.095 g, 0.52 mmol) (Example 3) and 85% H$_2$SO$_4$ (0.1 ml) was irradiated in a screw-capped tube using microwave radiation at 50 W for 1.5 minutes under nitrogen. To the resulting solution was added water (0.5 ml), saturated Na$_2$CO$_3$ (1 ml) and CH$_2$Cl$_2$ (2 ml) and the mixture transferred into a separating funnel. The aqueous phase was extracted with further portions of CH$_2$Cl$_2$ and the combined organic solutions washed with brine, dried (Na$_2$SO$_4$) and evaporated to yield a solid. Recrystallisation from EtOAc yielded 36 mg of a crystalline solid. $\delta_H$ (400 MHz, CDCl$_3$) 1.68–1.79 (2H, m), 1.97–2.03 (4H, m), 2.50–2.54 (2H, m), 2.71–2.75 (2H, m), 2.90–2.98 (1H, m), 3.06–3.09 (2H, m), 5.99 (1H, s), 6.66–6.67 (1H, m), 6.73–6.81 (2H, m), 7.09–7.15 (1H, m), 7.68–7.71 (1H, m), 7.77–7.79 (1H, m), 8.31–8.35 (1H, m).

EXAMPLE 10

1-[2-(2.4-Difluorophenyl)ethyl -4-[4-(2-methyltetrazol-5-yl)-phenylsulphonyl]piperidine A mixture of 4-(4-bromophenylsulphonyl)-1-[2-(2,4-difluorophenyl)ethyl]piperidine (0.38 g, 0.86 mmol), 2-methyl-5-(tributylstannyl)tetrazole (0.64 g, 1.72 mmol) and tetrakis(triphenylphosphine)palladium (100 mg, 0.02 mmol) in DMF was heated at 110° C. for 16 hours while stirring under nitrogen. The solution was poured into water/EtOAc (5/20 ml) and further extracted into EtOAc. The combined organic phase was washed with water, dried (Na$_2$SO$_4$) and evaporated to yield a syrup. Column chromatography (silica, EtOAc) followed by recrystallisation from EtOAc yielded 220 mg of crystalline material. $\delta_H$ (400 MHz, CDCl$_3$) 1.73–1.80 (2H, m), 1.98–2.06 (4H, m), 2.50–2.54 (2H, m), 2.71–2.75 (2H, m), 2.92–2.98 (1H, m), 3.05–3.08 (2H, m), 4.45 (3H, s), 6.71–6.80 (2H, m), 7.09–7.14 (1H, m), 7.99 (1H, d, J 5.2 Hz), 8.34 (1H, d, J 5.2 Hz).

EXAMPLE 11

1-[2-(2,4-Difluorophenyl)ethyl]-4-[4-(1-methyl-1,2,4-triazol-5-yl)-phenylsulphonyl]piperidine This compound was prepared analogously to Example 10 using 1-methyl-5-(tributylstannyl)-1,2,4-triazole. $\delta_H$ (400 MHz, CDCl$_3$) 1.70–1.80 (2H, m), 1.98–2.06 (4H, m), 2.51–2.55 (2H, m), 2.72–2.75 (2H, m), 2.92–2.98 (1H, m), 3.06–3.09 (2H, m), 4.06 (3H, s), 6.72–6.80 (2H, m), 7.09–7.12 (1H, m), 7.99–8.02 (2H, d, J 1.5 Hz), 8.02 (1H, s), 8.03–8.04 (2H, d, J 1.5 Hz).

EXAMPLE 12

1-[2-(2,4-Difluorophenyl)ethyl]-4-[4-(tetrazol-1-ylmethyl)phenylsulphonyl]piperidine a) 1-[2-(2,4-Difluorolphenyl)ethyl]-4-(4-methoxycarbonylphenylsulphonyl)piperidine 4-(4-Bromophenylsulphonyl)-1-[2-(2,4-difluorophenyl)ethyl]piperidine (2 g, 4.5 mmol) was stirred with Et$_3$N (1.25 ml, 9 mmol), 1,1'-bis(diphenylphosphino)ferrocene (0.15 g, 2.7 mmol) and Pd(OAc)$_2$ (0.03 g, 1.34 mmol) in a mixture of MeOH (10 ml) and DMF (20 ml) at 60° C. The mixture was allowed to stir at 60° C. under an atmosphere of carbon monoxide for 5 days, cooled to room temperature and concentrated. The residue was dissolved in CH$_2$Cl$_2$ and washed with water. The organic layer was dried (MgSO$_4$) and purified by column chromatography (SiO$_2$, EtOAc:pet. ether 60–80° 1:1) to give the product as a white solid, m.p. 123–124° C. (Found: C, 59.78; H, 5.52; N, 3.37. C$_{21}$H$_{23}$F$_2$NO$_4$S requires C, 59.56; H, 5.47; N, 3.31). $\delta_H$ (360 MHz, CDCl$_3$) 1.66–1.80 (2H, m), 1.96–2.02 (4H, m), 2.49–2.55 (2H, m), 2.72–2.78 (2H, m), 2.87–2.98 (1H, m), 3.03–3.10 (2H, m), 3.98 (3H, s), 6.71–6.81 (2H, m), 7.08–7.14 (1H, m), 7.96 (2H, d, J 8 Hz), 8.22 (2H, d, J 8 Hz).

b) 1-[2-(2,4-Difluorophenyl)ethyl]-4-(4-hydroxymethylphenylsulphonyl)piperidine 1-(2-(2,4-Difluorophenyl)ethyl]-4-(4-methoxycarbonylphenylsulphonyl)piperidine (0.6 g, 1.42 mmol) was dissolved in anhydrous CH$_2$Cl$_2$ (15 ml) and stirred under nitrogen at −78° C. DIBAL-H (1M in THF, 4.25 ml, 4.25 mmol) was added dropwise. The reaction mixture was stirred at −78° C. for 15 min, allowed to warm up to room temperature and stirred for 1 h. Crushed Na$_2$SO$_4$.10H$_2$O (5 eq.) was added and the mixture left at room temperature overnight. Inorganic solid was filtered off and washed with CH$_2$Cl$_2$ and EtOAc. The organic filtrate was concentrated to give a beige solid. $\delta_H$ (360 MHz, CDCl$_3$) 1.64–1.77 (2H, m), 1.94–2.06 (4H, m), 2.47–2.55 (2H, m), 2.70–2.76 (2H, m), 2.83–2.94 (2H, m), 3.02–3.08 (2H, m), 4.82 (2H, s), 6.71–6.82 (2H, m), 7.06–7.14 (1H, m), 7.55 (2H, d, 8 Hz), 7.85 (2H, d, 8 Hz).

c) 1-[2-(2,4-Difluorolphenyl)ethyl]-4-[4-(tetrazol-1-ylmethyl)-phenylsulphonyl]piperidine 1-[2-(2,4-Difluorophenyl)ethyl]-4-(4-hydroxymethylphenylsulphonyl)piperidine (0.20 g, 0.51 mmol) was dissolved in anhydrous THF (10 ml) under nitrogen at 0° C. Et$_3$N (0.14 ml, 1 mmol) and methanesulphonyl chloride (0.078 ml, 1 mmol) were added dropwise. The mixture was stirred at room temperature for 1 h, quenched with water aind extracted into EtOAc. The organic extracts were combined, washed with water, dried (MgSO$_4$) and solvent evaporated. The residue was dissolved in IPA (20 ml), and heated to reflux overnight with NaI (0.076 g), Cs$_2$CO$_3$ (0.197 g) and 1H-tetrazole (1.06 g, 15 mmol). The reaction mixture was cooled to room temperature and concentrated. The residue was partitioned between water and CH$_2$Cl$_2$ and the organic layer was washed with water, dried (MgSO$_4$) and concentrated. Purification by column chromatography (SiO$_2$; EtOAc:pet. ether 60–80° 1:1 to EtOAc-:MeOH 99:1) gave the title compound, m.p. 168–169° C. (Found: C, 56.00; H, 4.91; N, 15.82. C$_{21}$H$_{23}$N$_5$O$_2$SF$_2$ requires C, 56.36; H, 5.18; N, 15.63). $\delta_H$ (360 MHz, CDCl$_3$) 1.64–1.77 (2H, m), 1.97–2.05 (4H, m), 2.48–2.53 (2H, m), 2.70–2.76 (2H, m), 2.86–2.95 (1H, m), 3.01–3.10 (2H, m), 5.71 (2H, s), 6.72–6.80 (2H, m), 7.08–7.15 (1H, m), 7.46 (2H, d, J 8 Hz), 7.91 (2H, d, J 8 Hz), 8.65 (1H, s).

EXAMPLE 13

4-(4-Carboxamidophenylsulphonyl)-1-(2-phenylethyl)piperidine a) 4-(4-Bromophenylsulphonyl)-1-phenylacetamidopiperidine A solution of 4-(4-bromophenylsulphonyl)piperidine (Example 1, Step d) (1.0 g, 3.3 mmol), phenylacetic acid (674 mg, 5.0 mmol) and triethylamine (0.92 ml, 6.6 mmol) were stirred in $CH_2Cl_2$ (10 ml) under a nitrogen atmosphere. Bis(2-oxo-3-oxazolidinyl)phosphinic chloride (1.25 g,: 4.9 mmol) was added in portions and the reaction allowed to stir for 18 h. The reaction was washed sequentially with 1N HCl, saturated $Na_2CO_3$, brine and dried ($MgSO_4$). Concentration in vacuo gave the product as a colourless solid. $\delta_H$ (360 MHz, $CDCl_3$) 1.10–1.26 (1H, m), 1.40–1.55 (1H, m), 1.90–2.04 (2H, m), 2.48–2.55 (1H, m), 2.89–2.96 (1H, m), 3.00–3.10 (1H, m), 3.70–3.74 (2H, m), 3.94–3.98 (1H, m), 4.73–4.77 (1H, m), 7.15–7.17 (2H, m), 7.24–7.30 (3H, m), 7.63 (2H, d, J 6.48 Hz), 7.71 (2H, d, J 6.48 Hz).

b) 4-(4-Bromophenylsulphonyl)-1-(2-phenylethyl)piperidine

A suspension of the foregoing product (1.18 g, 2.8 mmol) in 20 ml anhydrous THF was stirred under a nitrogen atmosphere. $BH_3$:THF (13.9 ml of a 1.0M solution) was added and the reaction heated to reflux for 6 h. The reaction was allowed to cool, 6N HCl (50 ml) was added and the reaction allowed to stand for 18 h. The reaction was basified using 4N NaOH and extracted into $CH_2Cl_2$. The organic phase was washed with brine, dried ($Na_2SO_4$) and concentrated. Purification using dry flash column chromatography with 3% MeOH—$CH_2Cl_2$ as eluent gave the product as a solid. m/z ($ES^+$) 408 and 410 ($M+H^+$).

c) 4-(Carboxamidophenylsulphonyl)-1-(2-phenylethyl)piperidine

A suspension of the preceding product (0.86 g, 2.1 mmol) in 20 ml anhydrous DMF was degassed by passing a stream of nitrogen through for 10 minutes. Palladium(II) acetate (52 mg) and 1,3-bis(diphenylphosphino)propane (100 mg) were added. The reaction was purged with carbon monoxide before 1,1,1,3,3,3-hexamethyldisilazane (3.1 ml) and diisopropylamine (0.73 ml) were added. The reaction was heated to 100° C. under a CO atmosphere for 18 h. The reaction was allowed to cool and treated with 5N HCl (100 ml) for 4 h. The reaction was extracted with $Et_2O$. The aqueous phase was basified with 4N NaOH and extracted with, $Et_2O$ and then EtOAc. The combined organic phases were dried ($Na_2SO_4$), and concentrated to give the title compouid, m.p. 202–204° C. (MeOH). (Found: C, 64.06; H, 6.24; N, 7.14. $C_{20}H_{24}N_2O_3S$ requires C, 64.49; H, 6.49; N, 7.52). $\delta_H$ (400 MHz, $CDCl_3$) 1.67–1.78 (2H, m), 1.95–2.03 (4H, m), 2.54–2.58 (2H, m), 2.71–2.75 (2H, m), 2.89–2.97 (1H, m), 3.06–3.09 (2H, m), 6.00 (2H, br d, J 180 Hz), 7.14–7.20 (3H, m), 7.24–7.28 (2H, m), 7.94–7.99 (4H, m).

The following Examples were prepared, using the appropriate substituted phenylacetic acids, by the method described for Example 13:

EXAMPLE 14

4-(4-Carboxamidophenylsulphonyl)-1-[2-(4-fluorophenyl)ethyl]piperidine

Free base: m.p. 196–197° C. $\delta_H$ (400 MHz, $CDCl_3$) 1.69–1.77 (2H, m), 1.98–2.00 (4H, m), 2.52–2.54 (2H, m), 2.69–2.71 (2H, m), 2.90–2.93 (1H, m), 3.06–3.09 (2H, m), 5.68 (1H, s), 6.08 (1H, s), 6.95–6.97 (2H, m), 7.09–7.11 (2H, m), 7.98 (4H, s).

EXAMPLE 15

4-(4-Carboxamidophenylsulphonyl)-1-[2-(2-chlorophenyl)ethyl]piperidine

Free base: $\delta_H$ (400 MHz, $CDCl_3$) 1.70–1.78 (2H, m), 2.00–2.04 (4H, m), 2.52–2.58 (2H, m), 2.83–2.92 (3H, m), 3.07–3.10 (2H, m), 5.70 (1H, s), 6.10 (1H, s), 7.10–7.16 (3H, m), 7.18–7.21 (1H, m), 7.98 (4H, s).

EXAMPLE 16

4-(4-Carboxamidophenylsulphonyl)-1-(2-fluoro-2-phenylethyl)piperidine a) 4-(4-Bromophenylsulphonyl)-1-(2-fluoro-2-phenylethyl)piperidine 4-(4-Bromophenylsulphonyl)piperidine (0.7 g, 2.3 mmol) was reacted with α-fluorophenylacetic acid (0.53 g, 3.45 mmol) in a similar manner as described for Example 13, Steps a and b, to give the required product as a colourless solid, 0.56 g (58%), m.p. 126–127° C. (EtOAc-pet. ether 60–80°). $\delta_H$ (400 MHz, $CDCl_3$) 1.70–1.77 (2H, m), 2.00–2.03 (2H, m), 2.13–2.20 (2H, m), 2.57–2.69 (1H, m), 2.83–2.93 (2H, s), 3.04–3.18 (2H, m), 5.51–5.65 (1H, m), 7.28–7.39 (5H, m), 7.70–7.75 (4H, m).

b) 4-(4-Cyanophenylsulphonyl)-1-(2-fluoro-2-phenylethyl)piperidine 4-(4-Bromophenylsulphonyl)-1-(2-fluoro-2-phenylethyl)piperidine (0.69 g, 1.6 mmol) was dissolved in DMF (15 ml), and stirred with zinc cyanide (0.21 g, 1.79 mmol). The mixture was purged with nitrogen gas, tetrakis(triphenylphosphine)palladium(O) (80 mg) was added and the mixture heated at 80° C. for 4 hours. After cooling to room temperature, 10% aqueous $NH_4OH$ solution was added and the mixture was extracted with EtOAc. The organic extracts were combined, washed with saturated brine, water, dried ($MgSO_4$) and concentrated. The product was purified by column chromatography ($SiO_2$; MeOH:$CH_2Cl_2$ 2:98) to give the product as a colourless solid, m.p. 171° C. (EtOAc-pet. ether 60–80°). (Found: C, 64.36; H, 5.59; N, 7.37. $C_{20}H_{21}F_2N_2O_2S$ requires C, 64.50; H, 5.68; N, 7.52). $\delta_H$ (400 MHz, $CDCl_3$) 1.70–1.82 (2H, m), 1.99–2.02 (2H, m), 2.15–2.21 (2H, m), 2.57–2.70 (1H, m), 2.83–2.98 (2H, m), 2.05–3.08 (1H, m), 3.16–3.19 (1H, m), 5.50–5.65 (1H, m), 7.28–7.38 (5H, m), 7.87–7.89 (2H, d, J 8 Hz), 7.90–8.02 (2H, d, J 8 Hz).

c) 4-(4-Carboxamidophenylsulphonyl)-1-(2-fluoro-2-phenylethyl)piperidine 4-(4-Cyanophenylsulphonyl)-1-(2-fluoro-2-phenylethyl)piperidine (0.050 mg, 0.134 mmol) was dissolved in anhydrous THF (2 ml), and treated with potassium trimethylsilanolate (0.035 g, 0.369 mmol). The mixture was heated to reflux and the resultant precipitate was filtered off, dissolved in $CH_2Cl_2$, washed with water, dried ($MgSO_4$), and concentrated to give the title compound as a colourless solid, m.p. 192° C. $\delta^H$ (400 MHz, $CDCl_3$) 1.73–1.79 (2H, m), 1.99–2.03 (2H, m), 2.13–2.20 (2H, m), 2.56–2.96 (1H, m), 3.04–3.07 (1H, m), 3.15–3.18 (1H, m), 5.50–5.65 (1H, m), 7.26–7.38 (5H, m), 7.96–8.01 (4H, m).

EXAMPLE 17

1-[2-(2,4-Difluorophenyl)ethyl]-4-phenylsulphonylpiperidine

This compound was prepared following Example 1 Steps a–e using thiophenol in place of 4-bromothiophenol in Step b. $\delta_H$ (360 MHz, $CDCl_3$) 1.66–1.74 (2H, m), 1.96–2.04 (4H, m), 2.49–2.53 (2H, m), 2.71–2.75 (2H, m), 2.86–2.94 (1H, m), 3.04–3.08 (2H, m), 6.72–6.80 (2H, m), 7.09–7.14 (1H, m), 7.55–7.59 (2H, m), 7.64–7.68 (1H, s), 7.87–7.89 (2H, m).

EXAMPLE 18

4-(3-Carboxamidophenylsulphonyl)-1-[2-(2,4-difluorophenyl)ethyl]piperidine a) 4-(3-Bromophenylsulphonyl)-1-[2-(2,4-difluorophenyl)ethyl]piperidine

This compound was prepared following Example 1 Steps a–e using 3-bromothiophenol in place of 4-bromothiophenol in Step b. $\delta_H$ (360 MHz, CDCl$_3$) 1.66–1.74 (2H, m), 1.98–2.03 (4H, m), 2.50–2.54 (2H, m), 2.71–2.75 (2H, m), 2.87–2.94 (1H, m), 3.05–3.08 (2H, m), 6.72–6.80 (2H, m), 7.09–7.17 (1H, m), 7.45 (1H, t, 7.8 Hz), 7.78–7.82 (2H, m), 8.01–8.02 (1H, m).

b) 1-[2-(2,4-Difluorophenyl)ethyl]-4-(3-methoxycarbonylphenylsulphonyl)piperidine Carbon monoxide was bubbled through a solution of 4-(3-bromophenylsulphonyl)-1-[2-(2,4-difluorophenyl)ethyl]piperidine (3.95 g, 0.009 mol), Et$_3$N (2.5 ml, 0.018 mol), palladium(II) acetate (0.06 g, 0.0003 mol) and 1,1'-bis(diphenylphosphino)ferrocene (0.3 g, 0.0005 mol) in a mixture of methanol (30 ml) and DMF (30 ml) at room temperature. The mixture was heated at 60° C. for 18 h and then partitioned between ethyl acetate and water. Product from the organic phase was purified by column chromatography (SiO$_2$, EtOAc:pet. ether 60–80° C. 1:1) to give 2.75 g (73% yield) of material as a colourless solid, m.p. 116–117° C. $\delta_H$ (360 MHz, CDCl$_3$) 1.72–1.77 (2H, m), 1.97–2.03 (4H, m), 2.49–2.54 (2H, m), 2.70–2.75 (2H, m), 2.90–2.94 (1H, m), 3.04–3.07 (2H, m), 3.97 (3H, s), 6.72–6.80 (2H, m), 7.08–7.12 (1H, m), 7.67 (1H, t, 7.8 Hz), 8.07–8.50 (1H, m), 8.24–8.32 (1H, m), 8.55 (1H, s).

c) 4-(3-Carboxamidophenylsulphonyl)-1-2-(2,4-difluorophenyl)ethyl]piperidine A solution of 1-[2-(2,4-difluorophenyl)ethyl]-4-(3-methoxycarbonylphenylsulphonyl)piperidine (0.2 g, 0.00047 mol) in toluene (10 ml) was added to a mixture of trimethylaluminium (0.71 ml, 0.0014 mol) and ammonium chloride (0.077 g, 0.0014 mol) in toluene (8 ml) at 0° C. The mixture was heated at reflux for 18 h, cooled to room temperature and quenched with 2N HCl, basified with 2N NaOH and extracted with CH$_2$Cl$_2$. The crude product obtained from the organic phase was purified by column chromatography (SiO$_2$, CH$_2$Cl$_2$:MeOH 97:3) to give 41 mg (21% yield) of product, m.p. 142–143° C. $\delta_H$ (400 MHz, CDCl$_3$) 1.68–1.78 (2H, m), 1.97–2.02 (4H, mn), 2.50–2.54 (2H, m), 2.71–2.75 (2H, m), 2.90–3.00 (1H, m), 3.04–3.07 (2H, mn), 5.75–5.85 (1H, s), 6.20–6.30 (1H, s), 6.70–6.80 (2H, m), 7.10–7.15 (1H, m), 7.70 (1H, t, 7.8 Hz), 8.05 (1H, d, 7.8 Hz), 8.15 (1H, d, 7.8 Hz), 8.28 (1H, s).

EXAMPLE 19

4-(4-Bromophenylsulphonyl)-1-[2-(4-fluorophenyl)-2-oxoethl]piperidine 4-(4-Bromophenylsulphonyl)piperidine (Example 1 Step d, 0.9 g, 0.003 mol) was added to a mixture of 2-bromo-4'-fluoroacetophenone (0.7 g, 0.0033 mol) and potassium carbonate (0.84 g, 0.006 mol) in acetonitrile (5 ml) and the resulting slurry stirred at room temperature for 17 h. The insolubles were removed by filtration and the solvent evaporated to give a gum which was purified by column chromatography (SiO$_2$, CH$_2$Cl$_2$:MeOH 97:3) to give 0.5 g (36% yield) of product as a colourless solid. $\delta_H$ (400 MHz, CDCl$_3$) 1.75–1.90 (2H, m), 2.05–2.13 (2H, m), 2.25–2.40 (2H, m), 2.85–3.00 (1H, m), 3.04–3.20 (2H, m), 3.75–3.85 (2H, m), 7.12 (1H, t, 8 Hz), 7.24 (4H, s), 7.98–8.02 (2H, m).

EXAMPLE 20

4-(4-Cyanophenylsulphonyl)-1-[2-(4-fluorophenyl)-2-oxoethyl]piperidine

This compound was prepared following Example 1 Step f using 4-(4-bromophenylsulphonyl)-1-[2-(4-fluorophenyl)-2-oxoethyl]piperidine (Example 19) in place of 4-(4-bromophenylsulphonyl)-1-[2-(2,4-difluorophenyl)ethyl]piperidine. $\delta_H$ (360 MHz, CDCl$_3$) 1.75–1.86 (2H, m), 2.00–2.04 (2H, m), 2.19–2.25 (2H, m), 2.93–3.01 (1H, m), 3.06–3.09 (2H, m), 3.76 (2H, s), 7.12 (2H, t, 8 Hz), 7.87 (2H, d, 8 Hz), 7.98–8.01 (4H, m).

EXAMPLE 21

1-[2-(4-Fluorophenyl)-2-oxoethyl]-4-phenylsulphonylpiperidine

This compound was prepared following Example 19 using 4-phenylsulphonylpiperidine in place of 4-(4-bromophenylsulphonyl)piperidine. $\delta_H$ (400 MHz, CDCl$_3$) 1.75–1.85 (2H, m), 2.00–2.05 (2H, m), 2.19–2.22 (2H, m), 2.89–2.98 (1H, m), 3.05–3.08 (2H, m), 3.74 (2H, s), 7.12 (2H, t, 8 Hz), 7.56 (2H, t, 8 Hz), 7.65–7.69 (1H, m), 7.87 (2H, d, 8 Hz), 7.98–8.02 (2H, m).

EXAMPLE 22

1-[2-(4-Chlorophenyl)-2-oxoethyl]-4-phenylsulponylpiperidine

Prepared from 2-bromo-4'-chloroacetophenone utilising the method of Example 19. $\delta_H$ (400 MHz, CDCl$_3$) 1.76–1.87 (2H, m), 2.04–2.07 (2H, m), 2.21–2.26 (2H, m), 2.90–2.98 (1H, m), 3.07–3.10 (2H, m), 3.77 (2H, s), 7.42 (2H, d, 8 Hz), 7.56 (2H, t, 8 Hz), 7.65–7.69 (1H, m), 7.86–7.93 (4H, m).

What is claimed is:

1. A compound represented by formula IIA, or a pharmaceutically acceptable salt thereof:

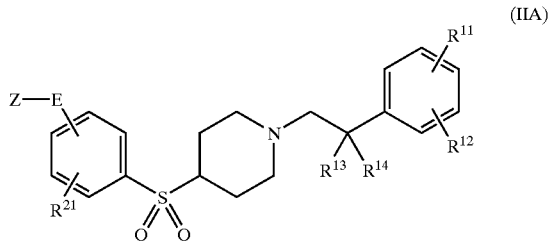

wherein

Z represents hydrogen, halogen, cyano, nitro, trifluoromethyl, trifluoromethoxy, —OR$^a$, —SR$^a$, —SOR$^a$, —SO$_2$R$^a$, —SO$_2$NR$^a$R$^b$, —NR$^a$R$^b$, —NR$^a$COR$^b$, —NR$^a$CO$_2$R$^b$, —COR$^a$, —CO$_2$R$^a$ or —CONR$^a$R$^b$;

R$^a$ and R$^b$ independently represent hydrogen or C$_{1-6}$ alkyl; or R$^a$ and R$^b$, when linked through a nitrogen atom, together represent the residue of an azetidine, pyrrolidine, piperidine or morpholine ring;

E represents a chemical bond or a straight or branched alkylene chain containing from 1 to 4 carbon atoms, optionally incorporating an oxygen atom to form an ether linkage;

$R^{11}$ and $R^{12}$ independently represent hydrogen, halogen, nitro, trifluoromethyl, $C_{1-6}$ alkyl, hydroxy, $C_{1-6}$ alkoxy, $C_{1-6}$ alkylthio or di($C_{1-6}$)alkylamino;

$R^{13}$ represents hydrogen and $R^{14}$ represents hydrogen or fluoro, or $R^{13}$ and $R^{14}$ together represent keto; and $R^{21}$ represents hydrogen or fluoro.

2. A compound as claimed in claim 1 represented by formula IIC, or a pharmaceutically acceptable salt thereof:

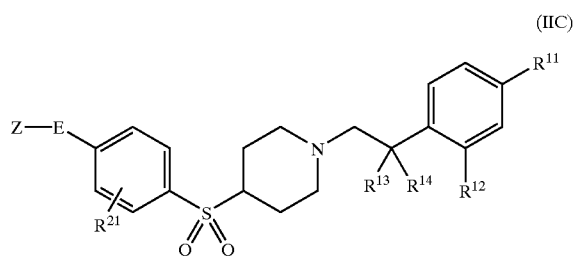

(IIC)

wherein Z, E, $R^{11}$, $R^{12}$, $R^{13}$, $R^{14}$ and $R^{21}$ are as defined in claim 1.

3. A compound selected from the group consisting of:

4-(4-cyanophenylsulphonyl)-1-[2-(2,4-difluorophenyl) ethyl]piperidine;
4-(4acetylaminophenylsulphonyl)-1-[2-(2,4-difluorophenyl)ethyl]piperidine;
4-(4cyano-3-fluorophenylsulphonyl)-1-[2-(2,4-difluorophenyl)ethyl]piperidine;
4-(4-carboxamidophenylsulphonyl)-1-[2-(2,4-difluorophenyl)ethyl]piperidine;
4-(4-carboxamido-3-fluorophenylsulphonyl)-1-[2-(2,4-difluorophenyl)ethyl]piperidine;
4-(4-carboxamidophenylsulphonyl)-1-(2-phenylethyl) piperidine;
4-(4-carboxamidophenylsulphonyl)-1-[2-(4-fluorophenyl) ethyl]piperidine;
4-(4-carboxarmidophenylsulphonyl)-1-[2-(2-chlorophenyl) ethyl]piperidine;
4-(4-carboxamidophenylsulphonyl)-1-(2-fluoro-2-phenylethyl)piperidine; and
1-[2-(2,4-difluorophenyl)ethyl]-4-phenylsulphonylpiperidine;
or a pharmaceutically acceptable salt thereof.

4. A compound selected from the group consisting of:
4-(3-carboxamidophenylsulphonyl)-1-[2-(2,4-difluorophenyl)ethyl]piperidine;
4-(4-bromophenylsulphonyl)-1-[2-(4-fluorophenyl)-2-oxoethyl]piperidine;
4-(4-cyanophenylsulphonyl)-1-[2-(4-fluorophenyl)-2-oxoethyl]piperidine;
1-[2-(4-fluorophenyl)-2-oxoethyl]-4-phenylsulphonylpiperidine; and
1-[2-(4-chlorophenyl)-2-oxoethyl]-4- phenylsulphonylpiperidine;
or a pharmaceutically acceptable salt thereof.

5. A pharmaceutical composition comprising a compound of formula IIA as defined in claim 1 or a pharmaceutically acceptable salt thereof in association with a pharmaceutically acceptable carrier.

6. A method for the treatment and/or prevention of a disorder for which a selective antagonist of the human 5-HT$_{2A}$ receptor is indicated, which comprises administering to a patient in need of such treatment an effective amount of a compound of formula IIA as defined in claim 1, or a pharmaceutically acceptable salt thereof.

7. A process for the preparation of a compound of Formula IIA as claimed in claim 1, which comprises one or both of steps (A) and (B):

(A) attachment of the moiety having the formula —(CH$_2$)(CR$^{13}$R$^{14}$)Phenyl, where Phenyl is substituted with R$^{11}$ and R$^{12}$, to a compound of formula VIII:

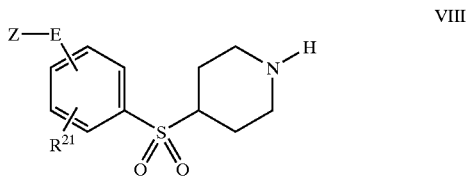

VIII wherein Z, E, $R^{11}$ $R^{12}$, $R^{13}$, $R^{14}$, and $R^{21}$ are as defined in claim 3; or (B) oxidizing a compound of formula IX:

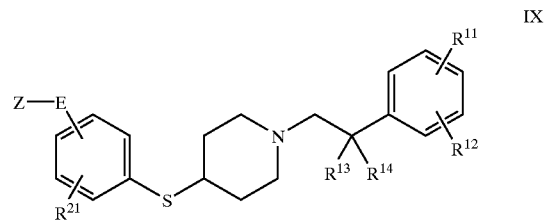

IX wherein Z, E, $R^{11}$ $R^{12}$, $R^{13}$, $R^{14}$, and $R^{21}$ are as defined in claim 3; and (C) subsequently, where required, converting a compound of formula IIA initially obtained into a further compound of formula IIA by conventional methods.

* * * * *